(12) United States Patent
Irie et al.

(10) Patent No.: US 6,657,094 B1
(45) Date of Patent: Dec. 2, 2003

(54) METHOD OF CHLORINATION OF END OF FLUORINE-CONTAINING COMPOUND

(75) Inventors: Masaki Irie, Settsu (JP); Kazuyoshi Kawasaki, Settsu (JP); Mitsuru Kishine, Settsu (JP)

(73) Assignee: Daikin Industries, Ltd., Osaka (JP)

( * ) Notice: Subject to any disclaimer, the term of this patent is extended or adjusted under 35 U.S.C. 154(b) by 11 days.

(21) Appl. No.: 10/088,736

(22) PCT Filed: Sep. 19, 2000

(86) PCT No.: PCT/JP00/06371

§ 371 (c)(1),
(2), (4) Date: Mar. 22, 2002

(87) PCT Pub. No.: WO01/21573

PCT Pub. Date: Mar. 29, 2001

(30) Foreign Application Priority Data

Sep. 24, 1999 (JP) .......................................... 11-269738

(51) Int. Cl.⁷ .......................... C07C 17/20; C07C 19/08
(52) U.S. Cl. ..................................................... 570/170
(58) Field of Search ........................ 570/170; 560/184; 204/157.88, 157.89, 157.95

(56) References Cited

U.S. PATENT DOCUMENTS 5,072,062 A * 12/1991 Kumai et al.

FOREIGN PATENT DOCUMENTS

JP   61-280446 A   12/1986
JP   63-303950 A   12/1988

OTHER PUBLICATIONS

Huang, Bing–Nan, et al., "Studies on polyhalolkanes II A facile method for mono–fluorination of α, ω–dihaloperfluoroalkanes", Chin. J. Chem., 1993, vol. 11, No. 2, p.174–177.

Chen, Loomis 2 et al., "Reaction of Phosphorus Pentachloride with Perhalo Carbonylcontaining Compounds", J. Fluorine Chem., 1989, vol. 42, No. 3, p 371–387.

* cited by examiner

Primary Examiner—Johann Richter
Assistant Examiner—Elvis O. Price
(74) Attorney, Agent, or Firm—Sughrue Mion, PLLC

(57) ABSTRACT

There is provided a method of end-chlorination of a fluorine-containing compound which can easily provide a fluorine-containing monomer having a functional group such as nitrile group at relatively low cost.

The method of chlorinating an end of a fluorine-containing compound having iodine atom at an end thereof comprises reacting a fluorine-containing organic compound having iodine atom at a molecular end thereof and represented by the formula (I):

$$RfCX_2I \qquad (I)$$

wherein Rf is an organic residue having fluorine atom, X is hydrogen atom or chlorine atom, with a chlorine gas at a temperature of from 150° C. to 180° C. under irradiation with light to cleave the C—I bond and replace iodine atom with chlorine atom.

5 Claims, No Drawings

METHOD OF CHLORINATION OF END OF FLUORINE-CONTAINING COMPOUND

This application is a 371 of PCT/JP00/06371, filed Sep. 19, 2000.

TECHNICAL FIELD

The present invention relates to a method of chlorinating an end of a fluorine-containing compound having iodine atom at an end thereof and to a novel compound obtained by the method. The compound is useful as a starting material for an ethylenically unsaturated fluorine-containing monomer having a functional group, for example, carboxyl group, nitrile group, or the like at an end thereof.

BACKGROUND ART

Fluorine-containing polymers are used in various forms such as a resin, elastomer, or the like in various fields since they possess specific properties, for example, water- and oil-repellency, heat resistance, chemical resistance, etc.

Further in the field of fluorine-containing resin, functioning thereof is made higher by introducing various functional groups. Also in the field of fluorine-containing elastomer, in order to improve crosslinkability (vulcanizability) and enhance physical properties after the crosslinking, various functional groups which become a crosslinking point are introduced.

For introducing the functional groups, there are, for example, a method of replacing a part of a trunk chain of the fluorine-containing polymer with a group containing a functional group, a method of modifying an end group of the fluorine-containing polymer to a functional group, a method of using a fluorine-containing monomer having functional group as a copolymerizing monomer, and the like.

In those methods, a monomer having a perfluorovinylether (—OCF=CF$_2$) exhibits good copolymerizability as the fluorine-containing monomer having a functional group which is used for the copolymerization method. However since an introduction of a double bond is difficult, synthesis thereof is complicated, a yield is not good and as a result, the obtained polymer is very expensive.

Also a compound having iodine atom at an end thereof is used as a fluorine-containing monomer having a functional group for forming a crosslinking point by utilizing such a property that iodine atom bonded to an end carbon atom is radically active. Such a fluorine-containing compound having —CH$_2$I group at an end thereof has a very strong bonding force between iodine atom and carbon atom, and therefore the C—I bond has been difficult to cleave. For that reason, with respect to a method for converting —CH$_2$I group of the fluorine-containing monomer to other functional group, only some limited reactions such as a de-IF reaction by Zn, or the like have been known.

On the other hand, attempts for chlorinating a fluorine-containing compound having iodine atom at an end thereof have been made (THE 14TH INTERNATIONAL SYMPOSIUM OF FLUORINE CHEMISTRY, pg. 168, 1994). That report says that when a fluorine-containing compound having iodine atom at an end thereof which is represented by the formula (Ia):

$$Rf^1CH_2I \quad (Ia)$$

wherein $Rf^1$ is a polyfluoroalkyl group, is reacted with chlorine gas, there is obtained a compound having iodine and chlorine atoms at an end thereof which is represented by the formula:

$$Rf^1CH_2ICl_2$$

wherein $Rf^1$ is as defined above, and the compound returns to the starting compound (Ia) at a temperature around a melting point thereof. Namely, even if the fluorine-containing compound having iodine atom at an end thereof is reacted with chlorine gas, it is impossible to cleave the C—I bond and replace iodine atom with chlorine atom. Furthermore, when heated, the compound is easily decomposed and returns to the starting compound.

An object of the present invention is to provide a novel method of cleaving an end C—I bond of a fluorine-containing compound having iodine atom, namely, a C—I bond at an end thereof and replacing iodine atom with chlorine atom. Another object of the present invention is to provide a novel fluorine-containing compound obtained only by the end-chlorination method of the present invention.

DISCLOSURE OF INVENTION

Namely, the present invention relates to a method of chlorinating an end of a fluorine-containing compound having iodine atom at an end thereof, which comprises reacting a fluorine-containing organic compound having iodine atom at a molecular end thereof and represented by the formula (I):

$$RfCX_2I \quad (I)$$

wherein Rf is an organic residue having fluorine atom, X is hydrogen atom or chlorine atom, with a chlorine gas at a temperature within a range of not less than 150° C. and preferably not more than the thermal decomposition temperature of the fluorine-containing organic compound.

Examples of the compound of the formula (I) which the chlorination method can be suitably applied on are a compound in which Rf is an organic residue which may have a functional group (for example, oxygen atom having ether bond, chlorine atom, carboxyl group, hydroxyl group, or the like) free from an effect of the chlorination and is a fluoroalkyl group having 1 to 15 carbon atoms and fluorine atoms having replaced a part or the whole of hydrogen atoms bonded to carbon atoms, and a compound in which Rf is an organic residue represented by the formula (II):

$$CH_3OC(=O)C(CF_3)F[OCF_2C(CF_3)F]_mOCF_2CF_2—$$

wherein m is 0 or an integer of from 1 to 3.

It is preferable that the chlorination reaction of the present invention is carried out under irradiation with light.

According to the end-chlorination method of the present invention, a novel fluorine-containing compound having a chlorinated end and represented by the formula (IV):

$$CCl_3CF_2CF_2O[C(CF_3)FCF_2O]_mC(CF_3)FCO_2CH_nCl_{3-n}$$

wherein n is 0, 1 or 2, m is 0 or an integer of from 1 to 3, can be prepared. With respect to the compound in which n is 0, an end group —CO$_2$CCl$_3$ is easily decomposed and is converted to a —COCl group.

BEST MODE FOR CARRYING OUT THE INVENTION

A fluorine-containing compound to be chlorinated by the present invention is the compound represented by the formula (I) in which one iodine atom is bonded to carbon atom at an end thereof. An atom bonded to the end carbon atom may be hydrogen atom or chlorine atom. Particularly, from the viewpoint of easiness of synthesis, the chlorination method can be suitably applied on a fluorine-containing compound having hydrogen atom.

The reaction of the present invention proceeds as far as Rf is in principle an organic residue in which at least one of hydrogen atoms bonding to carbon atoms has been replaced with fluorine atom. Rf may have a functional group such as oxygen atom having ether bond, chlorine atom, carboxyl group or hydroxyl group which is free from an effect of the chlorination. However since there is a fear of un-intended replacement of hydrogen atom, etc. with chlorine, preferred is a compound in which Rf is the above-mentioned polyfluoroalkyl group having 1 to 15 carbon atoms. Further since a fluorine-containing monomer precursor having —$CH_2I$ group can be formed into various fluorine-containing monomers having a functional group by chlorination thereof, the method of the present invention is useful for chlorination of an end of the compound having the organic residue represented by the formula (II).

Examples of the fluorine-containing compound (I) are, for instance,

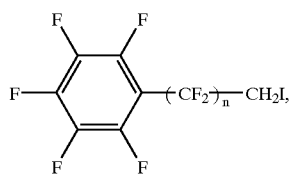

(n = 1 to 5)

(X=F or Cl), $ICH_2CF_2CF_2O[C(CF_3)FCF_2O]_mC(CF_3)FCH_2OH$, $ICH_2CF_2CF_2O[C(CF_3)FCF_2O]_mC(CF_3)FCOOH$, $ICH_2CF_2CF_2O[C(CF_3)FCF_2O]_mC(CF_3)FCO_2CH_3$, wherein m is 0 or an integer of from 1 to 3.

The fluorine-containing compound may be reacted with a chlorine gas at a temperature of not less than 150° C. and not more than the thermal decomposition temperature of the compound, for example, at a temperature of from 150° to 250° C., preferably from 150° to 180° C. When the reaction temperature is lower than 150° C., the C—I bond is not cleaved sufficiently and the chlorination does not proceed sufficiently. If the reaction temperature is more than 250° C., it is not preferable because a decomposition reaction of the starting compound arises.

The chlorination reaction can be carried out under irradiation with light if necessary. Though ultraviolet rays are preferable as the irradiation source, the reaction proceeds even with visible light or infrared rays. The irradiation of light is preferable since cleaving of the C—I bond and replacement of hydrogen atom with chlorine atom are accelerated.

The chlorine gas may be a highly pure chlorine gas or may be diluted with an inert gas (for example, nitrogen gas, argon gas, helium gas, or the like) into a concentration of about 10% to about 90%. Preferred is a highly pure chlorine gas.

An amount of the chlorine gas to be supplied is from 1 to 200 mole, preferably from 4 to 200 mole, more preferably from 5 to 50 mole, particularly preferably from 5 to 20 mole based on 1 mole of end carbon atom to be chlorinated.

The reaction time varies depending on reactivity of the starting compound, temperature, intensity of irradiation source, etc. and is usually from 1 to 200 hours, preferably from 5 to 50 hours. The longer the reaction time is, the more the chlorination rate is increased.

The reaction may be carried out under pressure, at ordinary pressure or under reduced pressure, and the reaction at ordinary pressure is preferable since a reactor made of glass is usually used.

The reaction may be carried out by heating to 150° to 250° C. while introducing the chlorine gas and then irradiating light or by irradiating light and then heating to 150° to 250° C. When an amount of the chlorine gas is too small, there is a case where a side reaction occurs.

In the chlorination method of the present invention, at an initial stage where the above-mentioned reaction conditions are reached, firstly, the C—I bond is cleaved and the chlorination occurs to form a C—Cl bond (—$CX_2Cl$). Then the chlorination proceeds and finally —$CCl_3$ end is formed. The released iodine atom is evaporated in the form of iodine chloride or iodine trichloride and then exhausted outside a system.

By the above-mentioned reaction, the iodine-containing end is partly or completely chlorinated and a fluorine-containing compound not having iodine atom can be obtained. In the present invention the end chlorination proceeds at a high chlorination rate (about not less than 90%), and a yield of the reaction product partly or completely chlorinated is not less than 80%, usually not less than 90%.

In the formula (I), in case where Rf has atoms, for example, oxygen atom, iodine atom, and the like other than atoms which are not chlorinated such as fluorine atom, chlorine atom and oxygen atom having an ether bond, there is a case where those atoms may be replaced with chlorine atoms.

The fluorine-containing compounds obtained by the end-chlorination method of the present invention encompass a novel compound. For example, the compound represented by the above-mentioned formula (IV) is a novel compound. For example, by carrying out the reaction in the manner mentioned below, an unsaturated fluorine-containing monomer having carboxyl group, hydroxyl group, ester group, amide group or nitrile group as a functional group can be prepared.

Through the decarboxylation reaction, a corresponding vinyl ether can be obtained by converting into a salt with sodium hydroxide or potassium hydroxide and then carrying out a thermal decomposition at a temperature of not less than 200° C. An end carboxyl group can be obtained according to YOUJI HUAXUE. 1998, 8, 439 to 440. Conversion into a nitrile group can be carried out according to U.S. Pat. No. 868,615 or JP-A-55-98212.

(1) End-chlorination Reaction of the Present Invention (Yield: About 90%)

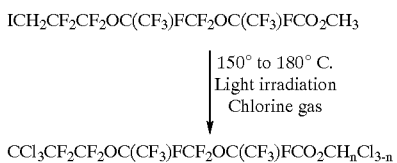

(2) Decarboxylation Reaction

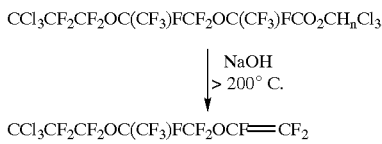

(3) End-carboxylation Reaction

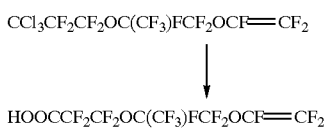

(4) Reaction for Conversion Into Nitrile

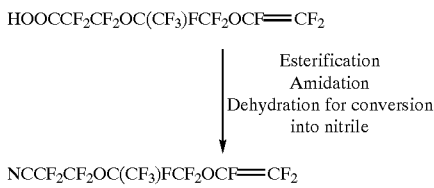

The present invention is then explained by means of examples, but is not limited to them.

EXAMPLE 1

A 50-ml three-necked flask equipped with a dry ice reflux condenser was charged with 50 g of a fluorine-containing compound represented by the formula: $ICH_2CF_2CF_2OC(CF_3)FCF_2OC(CF_3)FCO_2CH_3$ (purity: 96.4%, 82 mmol), and a chlorine gas was introduced while irradiating ultraviolet rays with a high pressure mercury lamp (available from Daika Kogyo Kabushiki Kaisha, output: 400W). An amount of chlorine gas was controlled so that a reflux speed would be about one drop per about 30 seconds of chlorine gas liquefied by the condenser.

Then a temperature of a reaction system was increased to 50° C. (5 hours), 80° C. (2 hours), 150° C. (5 hours) and 180° C. step by step. The reaction was carried out at 180° C. for 24 hours. A reaction product was sampled at final stages of each temperature and subjected to gas chromatograph mass spectrometry (GC-mass spectrometry) with model QP-1000A gas chromatograph mass spectrometer available from Shimadzu Corporation to determine the composition thereof. The composition of the reaction product was determined similarly three hours after, 13 hours after, 16 hours after and 24 hours after during the reaction at 180° C. A chlorination rate of the whole reaction product was calculated from the results of the determination. The results are shown in Table 1. Finally, 48 g of reaction product (colorless oily product) was obtained.

The reaction product was obtained in a state that compounds represented by:

$CH_pCl_{3-p}CF_2CF_2OCF(CF_3)CF_2OCF(CF_3)CO_2CH_nCl_{3-n}$ (n=0, 1, 2) were mixed. In Table 1, the product is identified by the number of p. In GC-mass spectrometry, when n is 0, $-CCl_3$ could not be detected and the end was detected in the form of $-COCl$. It is considered that this is because $-CCl_3$ released phosgene and $-COCl$ was formed.

Further each reaction product was esterified with methanol and identified through $^1$H-NMR and $^{19}$F-NMR analyses.

Fluorine-containing Compound of p=2

$^1$H-NMR: 3.9 ppm ($CH_2Cl$)

$^{19}$F-NMR: −82 ppm ($CF_3$), −84 ppm ($CF_2$), −85 ppm ($CF_3$), −128 ppm ($CH_2ClCF_2$), −134 ppm (CF), −147 ppm (CF)

GC-mass spectrum (m/e): 49 ($CH_2Cl$, compound of n=2), 83 ($CHCl_2$, compound of n=1), 63 (COCl, compound of n=0), 149 ($CH_2ClCF_2CF_2$), 315 ($CH_2ClCF_2CF_2OCF(CF_3)CF_2$)

Fluorine-containing Compound of p=1

$^1$H-NMR: 6.1 ppm ($CHCl_2$)

$^{19}$F-NMR: −82 ppm ($CF_3$), −84 ppm ($CF_2$), −85 ppm ($CF_3$), −122 ppm ($CHCl_2CF_2$), −134 ppm (CF), −147 ppm (CF)

GC-mass spectrum (m/e): 49 ($CH_2Cl$, compound of n=2), 83 ($CHCl_2$, compound of n=1), 63 (COCl, compound of n=0), 183 ($CHCl_2CF_2CF_2$), 349 ($CHCl_2CF_2CF_2OCF(CF_3)CF_2$)

Fluorine-containing Compound of p=0

$^1$H-NMR: None (no hydrogen atom)

$^{19}$F-NMR: −82 ppm ($CF_3$), −84 ppm ($CF_2$), −85 ppm ($CF_3$), −115 ppm ($Cl_3CF_2$), −134 ppm (CF), −147 ppm (CF)

GC-mass spectrum (m/e): 49 ($CH_2Cl$, compound of n=2), 83 ($CHCl_2$, compound of n=1), 63 (COCl, compound of n=0), 217 ($CCl_3CF_2CF_2$), 117 ($CCl_3$), 383 ($CCl_3CF_2CF_2OCF(CF_3)CF_2$)

TABLE 1

| Reaction temperature | Reaction time (hr) | | Reaction mixture (%) (Note 1) | | | | Chlorination rate (%) |
| --- | --- | --- | --- | --- | --- | --- | --- |
| | Actual time | Accumulated time | Starting compound | p = 2 | p = 1 | p = 0 | |
| 50° C. | 5 | 5 | 94.5 | 1.1 | 0 | 0 | 1 |
| 80° C. | 2 | 7 | 90.2 | 6.8 | 0 | 0 | 7 |
| 150° C. | 5 | 12 | 64.6 | 22.8 | 9.1 | 0 | 14 |

TABLE 1-continued

| Reaction temperature | Reaction time (hr) | | Reaction mixture (%) (Note 1) | | | | Chlorination rate (%) |
| --- | --- | --- | --- | --- | --- | --- | --- |
| | Actual time | Accumulated time | Starting compound | p = 2 | p = 1 | p = 0 | |
| 180° C. | 3 | 15 | 39.5 | 25.0 | 20.4 | 11.1 | 34 |
| 180° C. | 10 | 25 | 0 | 22.5 | 44.1 | 29.2 | 69 |
| 180° C. | 3 | 28 | 0 | 17.2 | 44.8 | 33.7 | 72 |
| 180° C. | 8 | 36 | 0 | 13.2 | 31.9 | 50.4 | 80 (Note 2) |

(Note 1) A purity of the starting compound was 96.4%.
(Note 2) The reaction was terminated when the chlorination rate was 80%.

As is clear from Table 1, it can be seen that when the reaction temperature became not less than 150° C., suddenly cleaving of the C—I bond arose and the chlorination proceeded.

EXAMPLE 2

A fluorine-containing compound having a chlorinated end was prepared in the same manner as in Example 1 except that the heating from room temperature to 180° C. was carried out at a temperature increasing rate of 1° C./min and the reaction was continued at 180° C. for ten hours. A composition and a chlorination rate of the reaction product were determined in the same manner as in Example 1. The results are shown in Table 2.

EXAMPLE 3

The reaction was carried out in the same manner as in Example 1 except that the irradiation with ultraviolet rays was not conducted, and the reaction product was identified in the same manner as in Example 1. The results are shown in Table 2.

TABLE 2

| | Reaction mixture (% by mole) | | | | Chlorination rate (%) |
| --- | --- | --- | --- | --- | --- |
| | Starting compound | p = 2 | p = 1 | p = 0 | |
| Ex. 2 | 38.4 | 24.2 | 22.4 | 11.8 | 36 |
| Ex. 3 | 97.1 | 0.7 | 0.4 | 0.1 | 0.6 |

As is clear from Table 2, it can be seen that in case where no light was irradiated, the chlorination rate was low but the C—I bond was cleaved and the chlorination arose. The chlorination rate may be increased by increasing the reaction time.

EXAMPLE 4

Chlorination was carried out at 180° C. for 100 hours under irradiation of the same light source as in Example 1 except that an amount of the starting compound was scaled up to 1,010 g (a 5-liter flask was used). The chlorination rate was 100% and the yield was 840 g.

COMPARATIVE EXAMPLE 1

The intermediate reaction mixture having a chlorination rate of 55% which was prepared in Example 4 was cooled to room temperature (25° C.) and subjected to irradiation with ultraviolet rays from the same light source as in Example 1 at room temperature for 30 hours. However no chlorination reaction occurred.

INDUSTRIAL APPLICABILITY

The present invention can provide a fluorine-containing compound having a chlorinated end from which a fluorine-containing monomer having a functional group can be prepared easily at relatively low cost. The present invention also can provide a chlorination method giving a fluorine-containing compound having a chlorinated end by easily chlorinating a fluorine-containing compound having iodine atom.

What is claimed is:

1. A method of chlorinating an end of a fluorine-containing compound having iodine atom at an end thereof, which comprises reacting a fluorine-containing organic compound having iodine atom at a molecular end thereof and represented by the formula (I):

RfCX$_2$I  (I)

wherein Rf is an organic residue which may have a functional group free from an effect of the chlorination and is a fluoroalkyl group having 1 to 15 carbon atoms and fluorine atoms having replaced a part or the whole of hydrogen atoms bonded to carbon atoms, X is hydrogen atom or chlorine atom, with a chlorine gas at a temperature within a range of not less than 150° C. and not more than a thermal decomposition temperature of the fluorine-containing organic compound to cleave the C—I bond and replace iodine atom with chlorine atom.

2. The method of end-chlorination of claim 1, wherein the reaction is carried out under irradiation with light.

3. A fluorine-containing compound having a chlorinated end which is represented by the formula (IV):

CCl$_3$CF$_2$CF$_2$O[C(CF$_3$)FCF$_2$O]$_m$C(CF$_3$)FCO$_2$CH$_n$Cl$_{3-n}$

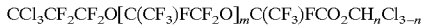

wherein n is 0, 1 or 2, m is 0 or an integer of from 1 to 3.

4. A method of chlorinating an end of a fluorine-containing compound having iodine atom at an end thereof, which comprises reacting a fluorine-containing organic compound having iodine atom at a molecular end thereof and represented by the formula (I):

RfCX$_2$I  (I)

wherein Rf is represented by the formula (II):

CH$_3$OC(=O)C(CF$_3$)F[OCF$_2$C(CF$_3$)F]$_m$OCF$_2$CF$_2$—  (II)

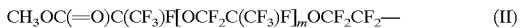

wherein m is 0 or an integer of from 1 to 3 and X is hydrogen atom or chlorine atom, with a chlorine gas at a temperature within a range of not less than 150° C. and not more than a thermal decomposition temperature of the fluorine-containing organic compound to cleave the C—I bond and replace iodine atom with chlorine atom.

5. The method of end-chloronation of claim 4, wherein the reaction is carried out under irradiation with light.

* * * * *